United States Patent [19]

Mattison et al.

[11] 3,939,203
[45] Feb. 17, 1976

[54] CERTAIN SUBSTITUTED 2-HYDROXYBENZOPHENOXIMES AND THE PROCESS OF EXTRACTING COPPER THEREWITH

[75] Inventors: Phillip L. Mattison, Minneapolis; Ronald R. Swanson, New Hope, both of Minn.

[73] Assignee: General Mills, Inc., Minneapolis, Minn.

[22] Filed: Mar. 18, 1968

[21] Appl. No.: 714,040

[52] U.S. Cl............ 260/566 A; 75/117; 260/429 C; 260/438.1
[51] Int. Cl.² .................................... C07C 131/00
[58] Field of Search ............... 260/566 A, 307 D

[56] References Cited
UNITED STATES PATENTS
3,428,449   2/1969   Swanson ............................. 75/117

FOREIGN PATENTS OR APPLICATIONS
799,742   8/1958   United Kingdom ................ 260/566

OTHER PUBLICATIONS

Beilstein's Handbuch der Organischen Chemie, Vol. 8, II Supplement, p. 183 (1948).

Blatt, J. Org. Chem. 20, pp. 591–602 (1955).

*Primary Examiner*—Gerald A. Schwartz
*Attorney, Agent, or Firm*—Gene O. Enockson

[57] ABSTRACT

Certain 2-hydroxy benzophenoximes containing an electron withdrawing substituent(s). Compositions comprised of such benzophenoximes and certain α-hydroxy aliphatic oximes. Compounds and compositions are useful for the extraction of metal values.

8 Claims, No Drawings

CERTAIN SUBSTITUTED 2-HYDROXYBENZOPHENOXIMES AND THE PROCESS OF EXTRACTING COPPER THEREWITH

The present invention relates to certain substituted 2-hydroxybenzophenoximes and the process of extracting copper values from aqueous solutions thereof using such new benzophenoximes.

It has recently been discovered that copper values can be recovered economically from certain aqueous leach liquors using a liquid ion exchange process employing particular phenolic oximes as the extractants. In this regard, percolation of water, with or without acid present, through waste dumps of low-grade copper containing rock yields dilute copper containing solutions, normally of copper sulfate. Such dilute copper sulfate liquors are usually close to pH 1.9–2.5 and contain relatively large amounts of ferric and ferrous iron relative to the copper. The phenolic oximes dissolved in an essentially water-immiscible organic solvent preferentially extract the copper values into the organic phase. Such values can then be stripped from the organic phase and recovered from the resulting concentrated strip solutions such as by electrolysis.

The phenolic oximes used prior to the present invention were those having the basic structure:

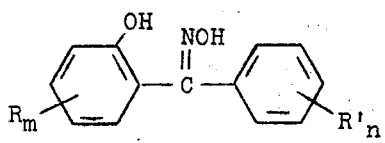

where R and R' are saturated aliphatic, ethylenically unsaturated aliphatic or saturated or ethylenically unsaturated aliphatic ether groups (i.e. —OR'') and $m$ and $n$ are 0, 1, 2, 3 or 4. The said phenolic oximes contain 3 to 25 carbon atoms in the R and R' groups, the latter being of 1 to 25 carbon atoms when saturated and 3 to 25 carbon atoms when ethylenically unsaturated.

While the above phenolic oximes were found to be effective as copper extractants over a wide pH range, their extraction efficiency drops off considerably when the aqueous copper containing solutions have pH's below about 1.5 and especially below about 1.0. Since certain leach liquors have very low pH's or develop low pH's on being subjected to liquid ion exchange extraction, it was considered to be a very desirable object to provide an extractant or extractants which would function with increased efficiency on such solutions. Certain concentrated copper solutions of very low pH are obtained by treatment of copper oxide ores with relatively strong acid leaching solutions. Further, in the ordinary extraction processes, hydrogen ions are exchanged for copper ions with the result that as extraction proceeds, the aqueous phase becomes more and more acidic. Consequently, for concentrated copper solutions, an extractant which is effective at very low pH ranges is needed.

We have now discovered a new group of compounds which are unexpectedly effective extractants for copper values from aqueous solutions thereof of low pH. These compounds generally have the formula as described above for the recently discovered phenolic oximes but in addition, have one or more electron withdrawing substituents on the ring containing the phenolic hydroxyl group, such electron withdrawing substituents substantially increasing the efficiency of the oxime compound as a copper extractant from low pH aqueous solutions—i.e. leach liquors. Our new compounds have the following structural formula:

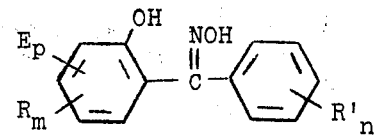

where R and R' are as defined above, E is an electron withdrawing substituent, $p$ is 1, 2, 3 or 4, $m$ is 0 or a whole integer up to 4-$p$ and $n$ is 0, 1, 2, 3 or 4. The electron withdrawing capacity of any particular substituent is proportional to the acid ionization constant of the corresponding phenol containing only such substituent. Phenol, itself, has an acid ionization constant, Ka, of about $1.1 \times 10^{-10}$ as variously reported in the literature (See "Organic Chemistry," 1959, by Robert Thornton Morrison and Robert Neilson Boyd, page 586). As such the substituents useful in our new compounds, provide substituted phenols with acid ionization constants of about $50 \times 10^{-10}$ and higher. In this regard, chloro in the para position yields a phenol having an acid ionization constant of only $6.3 \times 10^{-10}$ whereas orthochloro phenol has a Ka value of $77 \times 10^{-10}$. Accordingly, benzophenoximes substituted with a single chlorine in the para position to the hydroxyl group have essentially the same extraction efficiency as the corresponding unsubstituted compounds, and thus such chloro substituent can be considered as inert. The di and higher halogen substituted phenols have Ka values considerably above $50 \times 10^{-10}$. A preferred substituent is the nitro group, and especially good results are obtained when the said group is in the ortho or para position. Polynitro substituted phenols have high Ka values. Other representative useful electron withdrawing substituents are —CN, —SF$_5$, —SO$_2$R and the like where R is an organic radical such as an alkyl radical of 1 to 8 carbon atoms. The electron withdrawing group should not adversely affect the solubility or stability of the benzophenoxime and should not sterically hinder the OH group or cause interfering side reactions. Thus the reasonably bulky —SF$_5$ group would not be in the ortho position since it would sterically hinder the OH group. Likewise, the —NH$_2$ group in the meta position yields a substituted phenol having a Ka value of $69 \times 10^{-10}$. However, such group would interfere in the extraction process by complexing or reacting with the acid of the low pH copper containing solution.

The compounds of the present invention can be prepared by a number of methods. These routes involve the formation of the benzophenone followed by conversion of the benzophenone to the benzophenoxime, with the electron withdrawing substituents being introduced via starting materials or after formation of the benzophenone. Two illustrative methods of making the benzophenones include the following. The first such method is that reported by Newman (J. Org. Chem., 19, 985–1002, 1954). This method involves the reaction of a phenol with a benzotrichloride in accordance with the following equation:

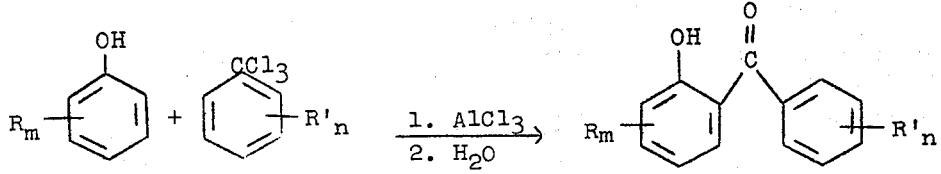

A second method involves the rearrangement where a phenolic ester is rearranged to a benzophenone in accordance with the following equation:

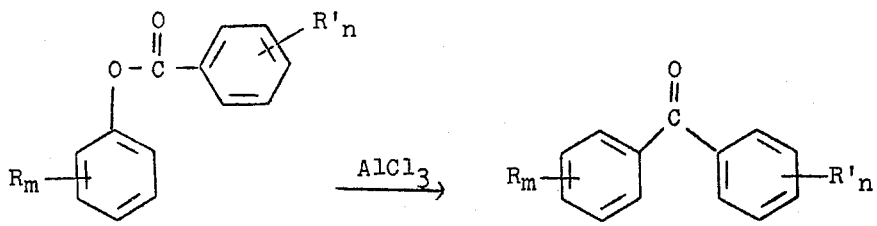

A third preferred method of producing the benzophenones is illustrated in the following sequence:

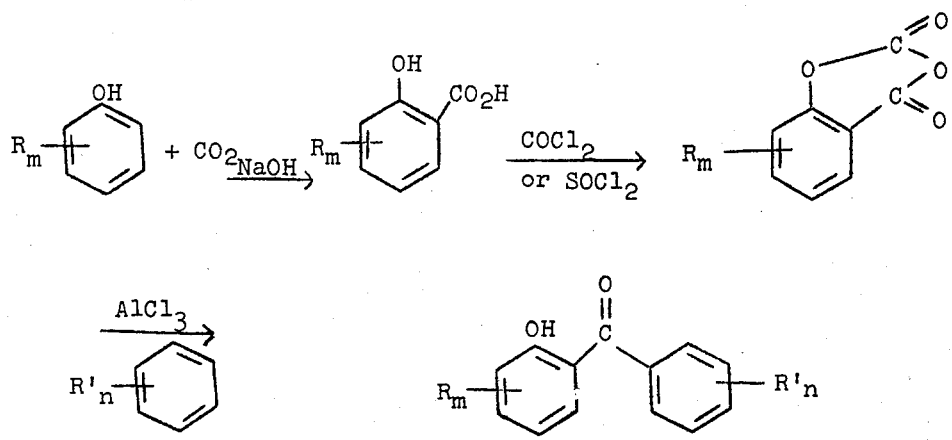

The starting phenol, benzotrichloride and the like in the above procedures may contain various radicals as R and R'. Representative of saturated radicals are methyl, ethyl, dimethylethyl, sec-butyl, tert-butyl, octyl, nonyl, decyl, dodecyl and the like. Branched chain alkyl groups are preferred over the straight chain groups. Various ethylenically unsaturated groups can also be used as R and R' and the same may be branched or straight chain. Representative of such groups are pentenyl, hexenyl, octenyl, dodecenyl, octadecenyl and the like. It is preferred that such groups contain less than about 2 double bonds and more preferably a single double bond. The R'' portion of the ether groups can be the saturated and ethylenically unsaturated aliphatic groups as described above. The R'' portion of the said ether groups is preferably an alkyl group. In addition, the saturated, ethylenically unsaturated and ether groups may contain inert substituents such as halogen, ester, amide and the like. The non-hydroxyl substituted aromatic nucleus of the benzophenoximes may also contain inert substituents. By inert is meant that the said substituents do not affect the solubility, stability or extraction efficiency of the compounds to any significant extent. Representative of aliphatic radicals containing inert substituents are

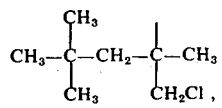

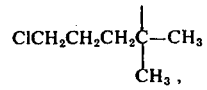

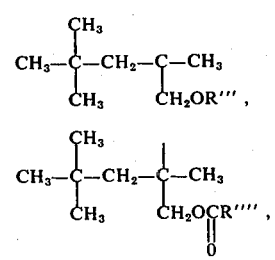

and the like where R''' and R'''' are alkyl groups of 1 to about 8 carbons for example.

In the above procedures, the electron withdrawing substituent may be introduced into the compound from the starting phenol. And as indicated the same can advantageously be introduced after the benzophenone is prepared. This latter method is preferred in preparing our compounds wherein the electron withdrawing group is the nitro group. Thus the corresponding benzophenone can be dissolved in a suitable solvent such as a mixture of acetic acid and acetic anhydride and fuming nitric acid added to cause nitration of the benzophenone.

The benzophenoximes of the present invention are prepared from the described benzophenones by reaction of the latter with a hydroxyl amine salt under reflux conditions. Such reaction can be carried out by refluxing the reactants in an alcohol such as methanol or ethanol and adding pyridine or sodium acetate to combine with the acid associated with the hydroxylamine.

As indicated, our new compounds are efficacious extractants for copper values having unexpected extraction efficiency under low pH conditions. In the process which also forms part of the present invention, the substituted benzophenoximes are dissolved in an essentially water-immiscible organic solvent which is contacted with the aqueous copper containing solution. A complex is formed between the copper values and the substituted benzophenoxime. Such complex is soluble in the organic solvent and thus the copper values are preferentially extracted into the said solvent. The organic phase is then separated from the aqueous phase and the copper values are stripped from the organic phase, usually be means of an acid. The organic phase containing the regenerated substituted benzophenoxime can be reused, such as by recycling, to contact further quantities of copper containing aqueous solutions. The copper values can be recovered as copper metal from the strip solution by electrolysis, for example.

The water-immiscible organic solvents preferably employed in our process are the aliphatic hydrocarbon solvents such as the petroleum-derived liquid hydrocarbons, either straight or branched chain, such as kerosene, fuel oil etc. Various aromatic solvents may also be used, such as benzene, toluene, xylene and others, for example, those derived from petroleum processing which may contain alkyl substituted aromatic materials. Typical of the latter solvents are those sold under the Panasol trademark by Amoco Chemicals Corporation, both in the "RX" and the "AN" series. These solvents are liquid and essentially insoluble in water. Generally, all these hydrocarbon solvents have specific gravities in the range of 0.65–0.95 and have a mid-boiling point in the approximate range of 120°–615°F. (ASTM Distillation). In addition to the simple hydrocarbon solvents, the chlorinated hydrocarbons may also be used and in some instances may improve solubility. Accordingly, both the unsubstituted and the chlorinated solvents are contemplated by the term "liquid hydrocarbon."

The substituted benzophenoximes of the present invention are further characterized as having sufficient solubility in one or more of the above solvents or mixtures thereof to make about a 2% by weight solution and as being essentially insoluble or immiscible with water. At the same time, the benzophenoxime should form a complex with the copper, which complex, likewise, is soluble in the essentially water-immiscible organic solvent to at least the extent of about 2% by weight. These characteristics are achieved by having alkyl, ethylenically unsaturated aliphatic or ether substituents as described on either ring. It is necessary to have substituents which total at least 3 carbon atoms. Usually, it is preferred not to have more than 25 carbon atoms total in the substituents since these substituents contribute to the molecular weight of the oxime without improving operability. Large substituents, therefore, increase the amount of oxime for a given copper loading capacity. In general, the branched chain alkyl substituents effect a greater degree of solubility of the reagent and of the copper complex and, accordingly, these are preferred. The compounds of the present invention are preferably used in an amount of about 2 to 50% by weight and more preferably about 5 to 15% by weight based on the weight of the organic phase.

The following examples illustrate preferred embodiments of the present invention without being limited thereto. Unless otherwise indicated, all parts and percentages are by weight.

EXAMPLE I

1. Preparation of 2-Hydroxy-3-nitro-5-dodecylbenzophenoxime

To a 5 liter round bottom flask equipped with a stirrer, thermometer and addition funnel were added 346.7 grams (2.6 mol) of aluminum chloride and 1900 ml. of carbon disulfide. The resulting mixture was cooled to 0°C. and then 524.8 grams (2 mol) of dodecylphenol (available from General Analine and Film—the dodecylphenol comprised a mixture of monoalkyl phenols, predominantly para substituted, the chains being random-branched alkyl radicals) mixed with 100 ml. of carbon disulfide were added at 0°C. to the flask. The flask was cooled to −15° to −20°C. Then 391 grams (2 mol) of benzotrichloride were added at temperatures of −15° to −20°C. over a period of 13 minutes. The flask was warmed to 0° to 5°C. and held for 1 hour at which time 1 liter of methanol was added at 0° to 5°C. followed by 500 ml. of water at the same temperatures. The mixture was heated and at 25°C. steam was passed through until a temperature of 100°C. was reached. The mixture was then cooled and poured into dilute hydrochloric acid and extracted with diethyl ether and dried over sodium sulfate. The solvent was stripped off and the residue was stripped and a fraction of 288.7 grams of 2-hydroxy-5-dodecylbenzophenone was recovered.

A solution of 70 grams of the 2-hydroxy-5-dodecylbenzophenone as prepared above in 60 ml. glacial acetic acid and 40 ml. acetic anhydride was charged to a 500 ml. round bottom flask equipped with a stirrer, thermometer and dropping funnel, and cooled by means of an ice bath to 15°C. Ten milliliters of fuming nitric acid was added dropwise with stirring over a 20 minute period at 20°–22°C. Stirring was continued at 15°–20°C. for an additional 20 minutes. The reaction mixture was poured into 200 ml. $H_2O$ and the mixture extracted three times with diethyl ether. The ether solution was washed with water, 5% aqueous $NaHCO_3$ and again with water. It was then dried over sodium sulfate and stripped of solvent to yield 76.1 grams of residue. Molecular distillation of 57.9 grams of this residue at 0.8 mm. Hg. and 210°C. gave 55.3 gm. of product which was 2-hydroxy-3-nitro-5-dodecylbenzophenone.

A mixture of 54.6 grams of 2-hydroxy-3-nitro-5-dodecylbenzophenone as prepared above, 18.5 grams hydroxylamine hydrochloride, 23.2 grams anhydrous sodium acetate and 100 ml. absolute methanol was charged to a 250 ml. round bottom flask equipped with a stirrer and reflux condenser. The reaction mixture was refluxed for 16 hours and then poured into 300 ml. water and extracted three times with Skellysolve B (a normal hexane solvent). The organic solution was washed with water, 5% aqueous $NaHCO_3$ and again with water. The hexane solvent was stripped from the product. There was thus obtained 55.4 grams of 2-hydroxy-3-nitro-5-dodecylbenzophenoxime.

2. Extraction of Copper

Mixtures of 10 ml. portions of a 5% wt./vol. solution of 2-hydroxy-3-nitro-5-dodecylbenzophenoxime in kerosene (50 grams of reagent diluted to 1 liter with kerosene), 5 ml. portions of a 6 gram/liter $Cu^{++}$ (as $CuSO_4 \cdot 5H_2O$) aqueous solution and 25 ml. of various aqueous acid or base solutions were shaken at ambient room temperature in 60 ml. separatory funnels for 10 minutes each. The layers were then separated and the organic phase was analyzed for copper and the pH of the aqueous phase was determined. The results are set forth in the following Table I.

Table I

| Extraction | Ml. Org. | Ml. $Cu^{++}$ | Ml. pH Adjuster | Final pH | ppm. $Cu^{++}$ in org. |
|---|---|---|---|---|---|
| A | 10 | 5 | 25-1.2M $H_2SO_4$ | 0.08 | 573 |
| B | 10 | 5 | 25-0.8M $H_2SO_4$ | 0.22 | 715 |
| C | 10 | 5 | 25-0.4M $H_2SO_4$ | 0.49 | 970 |
| D | 10 | 5 | 25-0.04M $H_2SO_4$ | 1.62 | 1320 |
| E | 10 | 5 | 25-$H_2O$ | 2.15 | 1425 |
| F | 10 | 5 | 25-0.008M $NaHCO_3$ | 2.52 | 1435 |
| G | 10 | 5 | 25-0.012M $NaHCO_3$ | 2.95 | 1490 |

The above data show that the compounds of the present invention are highly effective copper extractants at very low pH's. In comparison, the corresponding 2-hydroxy-5-dodecylbenzophenoxime under equivalent conditions extracted 18 ppm copper at 0.02 pH, 180 ppm copper at 0.50 pH, and 1010 ppm copper at 0.96 pH. Thus compounds of the present invention are surprisingly effective at very low pH's as compared to the compounds heretofore discovered. At higher pH's the 2-hydroxy-5-dodecylbenzophenoxime is more effective.

3. Extraction of Copper From An Aqueous $Cu^{++}$—$Fe^{+++}$ Solution

Part 1 was essentially repeated except that 10 ml. portions of the $Cu^{++}$ solution were used along with 10 ml. portions of a 6 gram/liter $Fe^{+++}$ (as $Fe_2(SO_4)_3$) aqueous solution and 10 ml. portions of various pH adjusters. The results are set forth in the following Table II.

Table II

| Extraction | Ml. Org. | Ml. $Cu^{++}$ | Ml. $Fe^{+++}$ | Ml. pH Adjuster | Final pH | ppm $Cu^{++}$ Org. | ppm $Fe^{+++}$ Org. |
|---|---|---|---|---|---|---|---|
| A | 10 | 10 | 10 | 10-1M $H_2SO_4$ | 0.50 | 1210 | 8 |
| B | 10 | 10 | 10 | 10-0.6M $H_2SO_4$ | 0.70 | 1300 | 10 |
| C | 10 | 10 | 10 | 10-0.1M $H_2SO_4$ | 1.50 | 1560 | 45 |
| D | 10 | 10 | 10 | 10-0.05M $H_2SO_4$ | 1.68 | 1580 | 46 |
| E | 10 | 10 | 10 | 10-$H_2O$ | 1.85 | 1620 | 48 |
| F | 10 | 10 | 10 | 10-0.05M $NaHCO_3$ | 2.12 | 1585 | 59 |

The above data show that the compounds of the present invention are not only excellent extractants for copper at very low pH's but in addition very selective. Thus the ratio of $Cu^{++}$ extracted to $Fe^{+++}$ at pH 0.50 is 151 and such ratio is still 27 at pH 2.12.

4. Stripping of $Cu^{++}$ From Loaded Organic Phase

Fifteen milliliter portions of a 5% wt./vol. solution of 2-hydroxy-3-nitro-5-dodecylbenzophenoxime in kerosene as used in part 2 loaded with 1540 ppm $Cu^{++}$ were shaken for varying times with 5 ml. portions of 10 and 30% by weight $H_2SO_4$ solutions. The phases were then separated, the organic analyzed for $Cu^{++}$ and the % $Cu^{++}$ stripped calculated. Results are set forth in the following Table III.

Table III

| Strip | Strip Solution | Time (min.) | % $Cu^{++}$ Stripped |
|---|---|---|---|
| A | 10% $H_2SO_4$ | ½ | 10 |
| B | " | 1 | 14 |
| C | " | 2 | 18 |
| D | " | 5 | 24 |
| E | 30% $H_2SO_4$ | ½ | 18 |
| F | " | 1 | 20 |
| G | " | 2 | 24 |
| H | " | 5 | 36 |

The above data indicate that even at an organic-:aqueous phase ratio of 3:1 and short contact times, a substantial proportion of the $Cu^{++}$ is stripped from the loaded organic phase.

EXAMPLE II

1. Preparation of a Mixture of 2-Hydroxy-3-nitro-4'-isopropylbenzophenoxime and 2-Hydroxy-5-nitro-4'-isopropylbenzophenoxime To a 500 ml. round bottom flask equipped with a stirrer, thermometer and condenser were charged 138 grams (1 mol) salicylic acid and ½ gram aluminum chloride. To this mixture was added 143 grams (1.2 mol) thionyl chloride and then the reactants were heated to 50°C. for 2½ hours with stirring. The excess thionyl chloride was removed at aspirator vacuum, the product cooled, and 180 grams (1.5 mol) cumene added thereto.

Three hundred seventy five ml. nitrobenzene and 159.5 grams aluminum chloride were added with mixing to a 2 liter round bottom flask equipped with a stirrer, thermometer and dropping funnel. The said mixture was cooled to 5°C. and then the above prepared acid chloride-cumene mixture was added slowly with stirring at 4°-8°C. over a 50 minute period. The resulting reaction mixture was slowly heated to 40°C. over a 1 hour period, the stirring was continued at 40° for 2 hours and then overnight (about 15 hours) at ambient room temperature. The mixture was poured onto about 750 grams ice and 150 ml. conc. HCl, and chloroform was added. It was boiled 15 minutes on a steam bath, cooled, the organic layer separated and the aqueous layer extracted with $CHCl_3$. The combined organic layer and $CHCl_3$ extraction solution was washed with water, 5% aqueous $Na_2CO_3$, water, and then saturated aqueous NaCl. It was dried and stripped on a rotary evaporator. Distillation of the residue up to 105° at 26 mm. Hg. gave 472.5 grams of a nitrobenzene-cumene mixture. The residue weighed 186.5 grams. The residue consisting of from 70–90% of the desired 2-hydroxy-4'-isopropylbenzophenone was distilled through a 15 in. Vigreaux column. The main collected fraction at 165°–167°C. and 2.25 mm. Hg was the desired product at substantially 100% purity.

A solution of 24 grams (0.1 mol) 2-hydroxy-4'-isopropylbenzophenone as prepared above in 16 ml. glacial acetic acid and 12 ml. acetic anhydride was added to a 100 ml. round bottom flask equipped with a thermometer, dropping funnel and stirrer. The solution was cooled to 5°C. by means of an ice bath and 6 ml. fuming nitric acid was added very slowly over a 50 minute period such that the temperature never rose past 10°C. After the addition was complete, the ice bath was removed, and in 10 minutes, the reaction had exothermed to 57°C. The cooling bath was returned and stirring at 20°C. was continued for 40 minutes after which the reaction mixture was poured onto ice. The mixture was extracted three times with ether and the combined ether solutions were washed with water, 5% aqueous $NaHCO_3$, water and saturated aqueous NaCl. The solution was then dried and stripped of ether giving 24.4 grams of a dark oil. This oil was molecularly distilled using pseudocumene as a heating liquid (168°C.). A tarry residue of 6.0 grams and a dark orange distillate (3.5 mm. Hg.) of 15.8 grams were obtained. Analysis of the distillate showed that it consisted mainly of a mixture of about 2 parts 2-hydroxy-3-nitro-4'-isopropylbenzophenone and 1 part 2-hydroxy-5-nitro-4'-isopropylbenzophenone.

Fourteen and one half grams (0.051 mol) of the above mixture were combined with 22 grams (0.316 mol) hydroxylamine hydrochloride, 28 grams (0.342 mol) anhydrous sodium acetate and 130 ml. absolute methanol in a 500 ml. round bottom flask equipped with a condenser, thermometer and stirrer. The reaction mixture was stirred at 63°C. overnight (about 16 hours) after which it was poured into 200 ml. water, cooled and extracted three times with ether. The ether extracts were washed with water to pH 5 and then with saturated aqueous NaCl. This was followed by drying and stripping off of the ether to yield 15.1 grams of a sticky yellow solid which was a mixture of the desired 3 and 5 nitro oximes.

2. Extraction of Copper

Twenty milliliter portions of an approximately 5% wt./vol. solution of the mixture of nitro oximes as above prepared in 1,1,2-trichloroethane (15 grams oxime and 285 ml. solvent), 10 ml. portions of a 6.35 gram/liter $Cu^{++}$ (as $CuSO_4.5H_2O$) aqueous solution having a pH of 1.90 (obtained by adding conc. $H_2SO_4$) and 10 ml. of various aqueous acid or base solutions were shaken at ambient room temperature in 60 ml. separatory funnels for two minutes each. The layers were then separated, the pH of the aqueous phase was determined and the aqueous phase was analyzed for copper content. The results are set forth in the following Table IV.

The above data shows that very good extraction is obtained at low pH values. In comparison, 2-hydroxy-4'-isopropylbenzophenoxime under the same conditions gave 3.5%, 27% and 40.6% extraction at 0.62 pH, 1.19 pH and 1.32 pH, respectively.

EXAMPLE III

1. Preparation of a Mixture of 2-Hydroxy-3-nitro-4'-dodecylbenzophenoxime and 2-Hydroxy-5-nitro-4'-dodecylbenzophenoxime One hundred thirty eight grams (1 mol) salicylic acid, 143 (1.2 mol) grams thionyl chloride and 0.25 gram aluminum chloride were combined in a 500 ml. round bottom flask equipped with a stirrer, condenser and thermometer. This reaction mixture was heated to 50°C. for 4.5 hours and then aspirator vacuum was applied to remove excess $SOCl_2$. After cooling, 356 grams (1.5 mol) dodecyl benzene (Neolene 400—the dodecyl groups are straight chain alkyl) were added and the mixture allowed to stand overnight. With cooling, 160 grams (1.2 mol) aluminum chloride were added to 375 ml. nitrobenzene in a 2 liter round bottom flask equipped with a thermometer, stirrer and dropping funnel. Such mixture was cooled to 5°C. and the above acid chloride-dodecylbenzene mixture added at 5°–8°C. over a 45 minute period. The resulting reaction mixture was slowly heated to 40°C. over a 2 hour period, stirred an additional 4 hours at such temperature and then overnight (about 16 hours) at ambient room temperature. It was then poured onto 500 grams ice, 150 ml. conc. HCl was added with stirring and the mixture was heated 20 minutes on a steam bath. The cooled mixture was extracted three times with ether, the combined ether extracts were washed with water to pH 3.5, then with 5% aqueous $NAHCO_3$, water and finally with saturated aqueous NaCl (three times). It was dried and stripped of ether giving 854 grams of a dark oil. Distillation at 24 mm. Hg. up to 116°C gave 446 grams red distillate and 389 grams residue. The residue was distilled through a 10 in. Vigreaux column to yield an 84 gram fraction at 175°–195°C. and 0.1 mm. Hg. which analyzed nearly 70% 2-hydroxy-4'-dodecylbenzophenone.

The above fraction along with 40 ml. glacial acetic acid and 30 ml. acetic anhydride were added to a 500 ml. round bottom flask equipped with a stirrer, thermometer, condenser and dropping funnel. The mixture was cooled to 5°C. and 11 ml. of fuming nitric acid was added with rapid stirring over a 45 minute period while maintaining the temperature at 5°–7°C. After an additional 15 minutes at 7°C., the reaction mixture was poured onto 100 grams ice and extracted three times with ether. The combined ether extracts were washed with water to pH 4 and then with 5% aqueous $NaHCO_3$. An emulsion formed so 10% aqueous HCl was added and the ether solution again washed with water to pH 4.

Table IV

| Extraction | Ml. Org. | Ml. $Cu^{++}$ | Ml. pH Adjuster | Final pH | $Cu^{++}$ Aq. g./l. | % $Cu^{++}$ Ex-* traction |
|---|---|---|---|---|---|---|
| A | 20 | 10 | 10-1M $H_2SO_4$ | 0.30 | 2.52 | 20 |
| B | 20 | 10 | 5-$H_2O$,5-1M $H_2SO_4$ | 0.55 | 2.14 | 32 |
| C | 20 | 10 | 8-$H_2O$,2-1M $H_2SO_4$ | 0.87 | 1.70 | 46.4 |
| D | 20 | 10 | 10-.1M $H_2SO_4$ | 1.05 | 1.39 | 56 |
| E | 20 | 10 | 10-.1 $NaHSO_4$ | 1.23 | 1.26 | 60 |
| F | 20 | 10 | 10-$H_2O$ | 1.33 | 1.06 | 66.4 |

*analysis of an extracted aqueous phase made up as F above showed 3.15 g./l. $Cu^{++}$ This was followed by three washings with saturated aqueous NaCl after which the extract solution was dried. The ether was vacuum stripped yielding 108.2 grams of a dark oil. The product consisted of about 50% of a mixture of 2-hydroxy-5-nitro-4'-dodecylbenzophenone and 2-hydroxy-3-nitro-4'-dodecylbenzophenone in a ratio of approximately 2:1.

Thirty eight grams of a mixture of the compounds as prepared above, 12.9 grams hydroxylamine hydrochloride, 16.1 grams anhydrous sodium acetate and 85 ml. absolute methanol were combined in a 250 ml. round bottom flask equipped with a stirrer, thermometer and condenser. The mixture was refluxed overnight, poured into water and extracted with Skellysolve B. The Skellysolve B layer, upon standing over a weekend, had a layer of insolubles in it. Water washing removed the insolubles, the same being suspended in the aqueous layer. The Skellysolve B phase was again washed with water, 5% aqueous $NaHCO_3$ and saturated aqueous NaCl. It was dried and stripped of solvent to yield 32.8 grams of the mixed 3 and 5 nitro oxime product.

2. Copper Extraction

A 5% wt./vol. solution of the mixed oxime prepared in part 1 in kerosene was used to extract copper from various aqueous solutions also containing $Fe^{+++}$. The extractions were carried out for 10 minutes at ambient room temperature in 60 ml. separatory funnels. The final or equilibrium pH was determined and the loaded organic phases were analyzed for $Cu^{++}$ and $Fe^{+++}$. The results are set forth in the following Table V.

40°C., maintained at 40°C. for 4 hours and stirred at room temperature overnight. The reaction mixture was then poured onto about 600 gm. of ice and 300 ml. conc. HCl and stirred in a steam bath for one-half hour. It was then extracted 3 times with Skellysolve B and the organic layer washed with water to pH 3, 3 times with 5% aqueous $NaHCO_3$, water and saturated aqueous NaCl. It was dried and stripped of solvent and predistilled to yield a residue weighing 514.0 grams. This residue was distilled through a 30 in. Vigreaux column to yield several fractions including an 86.5 gram fraction at 0.45–0.7 mm. Hg., pot temperature of 274°–288°C. and vapor temperature of 210°–217°C. Analysis showed that this fraction consisted of 68% of 2-hydroxy-3-methyl-4'-dodecylbenzophenone.

To a 500 ml. round bottom flask were added 75 grams of the benzophenone as prepared above, 150 ml. glacial acetic acid and 75 ml. acetic anhydride. This mixture was cooled to about 15°C. and then 9.5 ml. of fuming nitric acid was added over a 10 minute period at 13°–17°C. The cooling bath was removed and the reaction slowly exothermed to 32°C. over 10 minutes. The mixture was then poured onto ice and extracted with Skellysolve B. The organic layer was washed with water, 5% aqueous $NaHCO_3$, water, saturated aqueous NaCl, dried and stripped of solvent giving 81.3 grams of a dark oil. Molecular distillation at 0.2 mm. Hg. using aniline as the heating medium, gave a residue (tarry) of 10.7 grams, and a distillate in two fractions: 42.5 grams and 12.0 grams. Both fractions consisted essentially of 2-hydroxy-3-methyl-5-nitro-4'-dodecylbenzophenone.

Table V

| Extraction | Org. Ml. | $Cu^{++}$ Sol. | Aqueous* (Ml.) $Fe^{+++}$ Sol. | Additive | Final pH | $Cu^{++}$ ppm Org. | $Fe^{+++}$ ppm Org. |
|---|---|---|---|---|---|---|---|
| A | 10 | 5 | 5 | 20-$H_2O$ | 1.82 | 2100 | 143 |
| B | 10 | 5 | 5 | 5-.1M $NaHCO_3$ 15-$H_2O$ | 2.22 | 2115 | 165 |
| C | 10 | 5 | 5 | 20-.1M $H_2SO_4$ | 1.30 | 1790 | 90 |
| D | 10 | 5 | 5 | 5-2M $H_2SO_4$ 15-$H_2O$ | 0.40 | 888 | 40 |
| E | 10 | 5 | 5 | 10-2M $H_2SO_4$ 10-water | 0.08 | 615 | 30 |

*The copper solution contained 5.95 g./l. $Cu^{++}$ (prepared by diluting 23.58 grams $CuSO_4.5H_2O$ with water). The $Fe^{+++}$ solution contained 6.64 g./l. $Fe^{+++}$ (prepared by diluting 29.28 grams $Fe_2(SO_4)_3.XH_2O$ with water). The aqueous phases were made up to 30 ml. by the various additive solutions.

EXAMPLE IV

1. Preparation of 2-Hydroxy-3-methyl-5-nitro-4'-dodecylbenzophenoxime

Three hundred four grams (2 mol) of 3-methyl salicylic acid, 225 ml. (3.1 mol) thionyl chloride and ½ gram $AlCl_3$ were combined in a 2 liter round bottom flask and stirred while heating from 25° to 50°C. over a 2½ hour period. Stirring at 50°C. was continued for 2 more hours and then aspirator vacuum was applied to remove the excess $SOCl_2$. To the residue was added 845 ml. (729 grams, 3 mol) of dodecyl benzene (AB 515 available from Conoco—the dodecyl groups are random-branched alkyl groups).

Seven hundred fifty ml. nitrobenzene was charged to a 5 liter round bottom flask and then 333 grams (2.5 mol) aluminum chloride were added thereto with cooling and stirring. When this mixture reached 10°C., the above dodecyl benzene-acid chloride combination was added over 20 minutes by a dropping funnel. Then the reaction mixture was slowly heated over 2 hours to Fifty-two grams of the above-prepared benzophenone were combined with 18.0 grams hydroxylamine hydrochloride, 22.4 grams anhydrous sodium acetate and 110 ml. absolute methanol in a 250 ml. round bottom flask and stirred under reflux overnight. The reaction mixture was poured into 200 ml. water and extracted three times with Skellysolve B. After standing a few minutes, a bulky precipitate formed in the organic extractant. It dissolved upon the addition of a small amount of ether. The organic phase was then washed with water, 5% aqueous $NaHCO_3$, water, saturated aqueous NaCl, dried and stripped of solvent giving 53.3 grams semi-solid product consisting of about 90% of 2-hydroxy-3-methyl-5-nitro-4'-dodecylbenzophenoxime and about 10% of the starting benzophenone.

2. Copper Extraction

Part 2 of Example III was essentially repeated except that 2-hydroxy-3-methyl-5-nitro-4'-dodecylbenzophenoxime was used as the extractant. The results are set forth in the following Table VI.

Table VI

| Extraction | Org. Ml. | $Cu^{++}$ Sol. | $Fe^{+++}$ Sol. | Aqueous (Ml.) Additive | Final pH | $Cu^{++}$ ppm Org. | $Fe^{+++}$ ppm Org. |
|---|---|---|---|---|---|---|---|
| A | 10 | 5 | 5 | 20-water | 1.70 | 500 | 104 |
| B | 10 | 5 | 5 | 5-.1M $NaHCO_3$ 15-water | 2.02 | | |
| C | 10 | 5 | 5 | 20-1M $H_2SO_4$ | 1.10 | 305 | 66 |
| D | 10 | 5 | 5 | 5-2M $H_2SO_4$ 15-water | 0.49 | 250 | 50 |
| E | 10 | 5 | 5 | 10-2M $H_2SO_4$ 10-water | 0.22 | 345 | 36 |

The compounds of the present invention can also be used in combination with other extractants where desired and, in particular, with certain α-hydroxy aliphatic oximes. The latter compounds can further improve the kinetics of the extraction at low pH's without any serious effect on the selectivity of the extraction with respect to iron.

The α-hydroxy oxime extractants which may be used for this purpose have the following general formula:

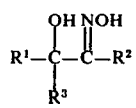

where $R^1$, $R^2$ and $R^3$ may be any of a variety of organic radicals such as aliphatic and alkylaryl radicals. $R^3$ may also be hydrogen. Preferably, $R^1$ and $R^2$ are unsaturated hydrocarbon or branched chain alkyl groups containing from about 6 to 20 carbon atoms. $R^1$ and $R^2$ are also preferably the same and when alkyl are preferably attached to the carbons substituted with the —OH and =NOH groups through a secondary carbon atom. It is also preferred that $R^3$ is hydrogen or unsaturated hydrocarbon or branched chain alkyl groups containing from about 6 to 20 carbon atoms. The α-hydroxy oximes also preferably contain a total of about 14 to 40 carbon atoms. Representative compounds are 19-hydroxyhexatriaconta-9,27-dien-18-oxime, 5,10-diethyl-8-hydroxytetradecan-7-oxime, and 5,8-diethyl-7-hydroxydodecane-6-oxime. The latter compound has the following structural formula:

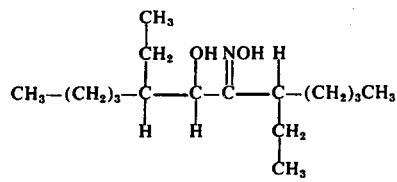

Representative of other mono- and polyunsaturated radicals are heptenyl, octenyl, decenyl, octadecenyl, octadecynyl, and alkyl substituted radicals such as ethyloctadecenyl. Representative of other mono- and polyalkyl substituted saturated radicals are ethylhexyl, diethylheptyl, butyldecyl, butylhexadecyl, ethylbutyldodecyl, butylcyclohexyl and the like. The R', R'' and R'''groups may contain inert substituents.

The α-hydroxy oxime extractants are also characterized as having a solubility of at least 2% by weight in the water-immiscible organic solvent used to make up the organic phase and substantially complete insolubility in water. In addition, it is believed that the copper values and the α-hydroxy oxime extractant form a complex during the initial extraction step and such complex, when formed, should also have a solubility of at least 2% by weight in the hydrocarbon solvent.

The relative amounts of the compounds of the present invention and the said α-hydroxy aliphatic oximes can be varied widely. Even minute quantities of the α-hydroxy aliphatic oxime can be beneficial. However, a preferred range is 1 to 100% by weight of the α-hydroxy aliphatic oxime based on the weight of the compounds of the present invention, with an especially preferred range being 15–50% by weight. In general, the concentration of total oxime is in the range of about 2–25%, based on the weight of the organic extracting solution.

The embodiments of the invention in which an exclusive property or privilege is claimed are defined as follows:

1. A compound of the formula

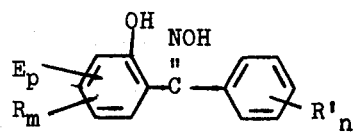

in which R and R' may be individually alike or different and are saturated aliphatic hydrocarbon groups of 1–25 carbon atoms, E is an electron withdrawing substituent, $p$ is 1, 2, 3 or 4, $m$ is 0 or a whole integer up to 4-$p$ and $n$ is 0, 1, 2, 3 or 4, said compound having a total of 3–25 carbon atoms in $R_m$ and $R'_n$ and said electron withdrawing substituent $E_p$ (1) having an electron withdrawing capacity such that a phenol containing only said substituent has an acid ionization constant Ka of at least about 50 × $10^{-10}$ and (2) being so selected and positioned on the aromatic ring to substantially increase the efficiency of the compound as a copper extractant from aqueous solutions having a pH of less than about 1.0.

2. A compound according to claim 1 in which R' is a branched chain aliphatic hydrocarbon group.

3. A compound according to claim 1 in which R is a branched chain aliphatic hydrocarbon group.

4. A compound according to claim 1 in which the electron withdrawing substituent is a nitro group.

5. 2-Hydroxy-3-nitro-5-dodecylbenzophenoxime.

6. 2-Hydroxy-3-nitro-4'-isopropylbenzophenoxime.

7. 2-Hydroxy-5-nitro-4'-isopropylbenzophenoxime.

8. 2-Hydroxy-3-methyl-5-nitro-4'-dodecylbenzophenoxime.

* * * * *